(12) United States Patent
Werner

(10) Patent No.: US 10,653,531 B2
(45) Date of Patent: May 19, 2020

(54) PROSTHETIC DEVICE

(71) Applicant: WERNER CONSULTING AG, Wollerau (CH)

(72) Inventor: Clément Werner, Männedorf (CH)

(73) Assignee: WERNER CONSULTING AG, Wollerau (CH)

( * ) Notice: Subject to any disclaimer, the term of this patent is extended or adjusted under 35 U.S.C. 154(b) by 154 days.

(21) Appl. No.: 15/736,984

(22) PCT Filed: Jun. 23, 2016

(86) PCT No.: PCT/EP2016/064534
§ 371 (c)(1),
(2) Date: Dec. 15, 2017

(87) PCT Pub. No.: WO2017/001278
PCT Pub. Date: Jan. 5, 2017

(65) Prior Publication Data
US 2018/0368983 A1    Dec. 27, 2018

(30) Foreign Application Priority Data

Jun. 30, 2015  (EP) ..................... 15174528

(51) Int. Cl.
*A61F 2/44*   (2006.01)
*A61F 2/30*   (2006.01)

(52) U.S. Cl.
CPC .... *A61F 2/442* (2013.01); *A61F 2002/30075* (2013.01); *A61F 2002/30077* (2013.01);
(Continued)

(58) Field of Classification Search
None
See application file for complete search history.

(56) References Cited

U.S. PATENT DOCUMENTS

| 6,015,436 A | 1/2000 | Schonhoffer |
| 2004/0049271 A1 | 3/2004 | Biedermann et al. |

(Continued)

FOREIGN PATENT DOCUMENTS

| EP | 2777632 A1 | 9/2014 |
| WO | 2005/112834 A2 | 12/2005 |
| WO | 2009/105182 A1 | 8/2009 |

OTHER PUBLICATIONS

Sep. 2, 2016 International Search Report issued in International Application No. PCT/EP2016/064534.

*Primary Examiner* — Sameh R Boles
(74) *Attorney, Agent, or Firm* — Oliff PLC

(57) ABSTRACT

A prosthetic device for replacing at least part of one vertebral body, the prosthetic device being expandable from a fully collapsed state to a fully expanded state and comprising an upper endplate, a lower endplate and an expandable support structure extending between the two endplates, said expandable support structure being configured to displace the two endplates relative to one another along a longitudinal axis of the prosthetic device and to hold the two endplates at a minimum axial distance that corresponds to the height of at least one intervertebral disc and half a vertebral body, wherein the expandable support structure includes an anterior post and a posterior post, wherein the length (L1/L2) of each post is individually adjustable and is lockable independently from one another to hold the two endplates with an inclination of 0° to 40° relative to each other.

18 Claims, 6 Drawing Sheets

Figure 1:
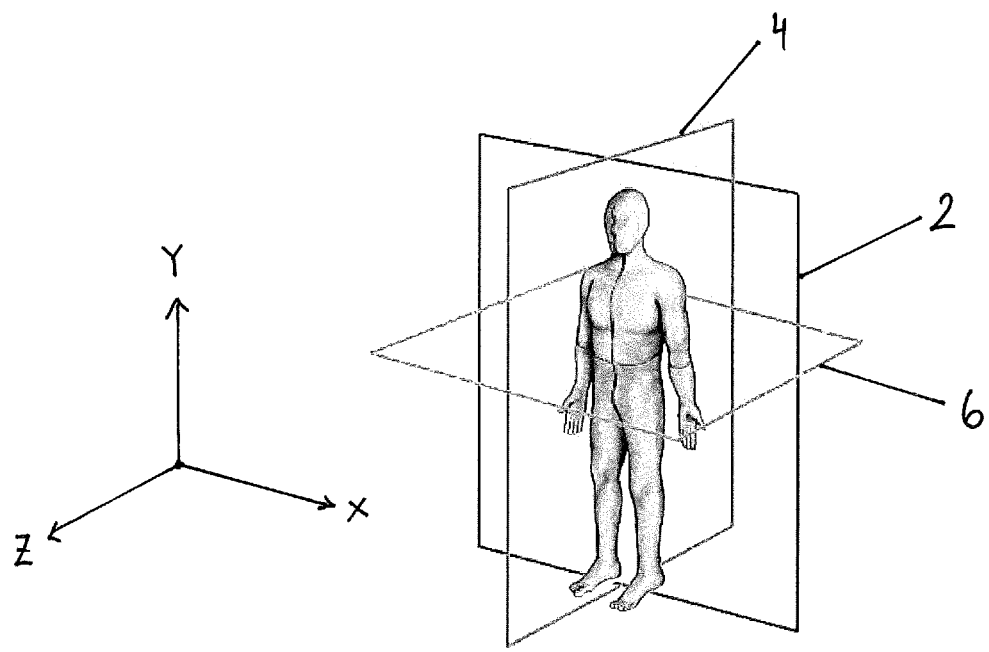

(52) U.S. Cl.
CPC ............... *A61F 2002/30166* (2013.01); *A61F 2002/30395* (2013.01); *A61F 2002/30471* (2013.01); *A61F 2002/30484* (2013.01); *A61F 2002/30538* (2013.01); *A61F 2002/30556* (2013.01); *A61F 2002/30565* (2013.01); *A61F 2002/30579* (2013.01); *A61F 2002/443* (2013.01)

(56) References Cited

U.S. PATENT DOCUMENTS

| | | |
|---|---|---|
| 2005/0113921 A1 | 5/2005 | An et al. |
| 2005/0256576 A1 | 11/2005 | Moskowitz et al. |
| 2007/0250172 A1* | 10/2007 | Moskowitz ............. A61F 2/442 623/17.15 |
| 2008/0167718 A1 | 7/2008 | Protopsaltis |
| 2009/0216331 A1 | 8/2009 | Grotz et al. |
| 2009/0270987 A1 | 10/2009 | Heinz et al. |
| 2012/0197403 A1 | 8/2012 | Merves |
| 2014/0156006 A1 | 6/2014 | Bannigan et al. |

* cited by examiner

PROSTHETIC DEVICE

The present invention relates to a prosthetic device for replacing a vertebral body according to the preamble of Claim 1.

When a vertebral body is collapsed, damaged or unstable due to tumor, infection or trauma (i.e. fracture), the vertebral body or a portion thereof may need to be removed (full or partial corpectomy) and replaced by a prosthetic device in order to alleviate pain and spinal cord decompression, stabilize the vertebrae and facilitate anatomical recovery. Corpectomy is often performed in association with some form of discectomy, i.e. surgical removal of at least part of an intervertebral disc.

In recent years, various types of such vertebral body replacement devices or "spine implants" have been developed for replacement of at least part of one vertebral body and the adjacent intervertebral disc(s). Typically, these implants are manufactured at various heights in order to fit within a cavity that remains after having removed the damaged vertebral material.

The majority of vertebral body replacement devices are designed to be introduced through a direct anterior, antero-lateral or direct lateral approach channel that is perpendicular to the spinal column, with the implant itself oriented parallel with the axis of the spine.

Despite the use of imaging control, e.g. by X-ray, CT or MRI, the fitting of the implant within the patient's spine presents a serious challenge to the surgeon. In particular, apart from correct positioning of the implant in situ, also the size and configuration of the implant need to be chosen to fit the patient's anatomy to achieve secure anchorage of the implant within the spinal defect. Specifically, if the implant is too big, it may be damaged or it may damage the remaining vertebral bodies during implantation. On the other hand, if the implant size is too small, there is a high risk of dislocation due to imperfect fitting. In addition, given that the vertebrae are not, at the time of implantation, in an anatomical position, it is difficult to determine the required implant dimensions.

In order to facilitate the fitting of the implant into the cavity created by a corpectomy procedure, implants have been developed which are expanded in situ and held in place by a press fit between the vertebral bodies. Such implant devices are described, e.g. in US 2004/0049271, US 2005/0113921, US 2012/0197403 or U.S. Pat. No. 6,015,436. These implant devices usually have one central post that can be expanded along the central longitudinal axis of the device. This way the implant can be fitted in place by the surgeon, then extended and locked in situ to support the adjacent vertebral bodies and it may even distract the distance between the latter.

For providing a strong interface between the vertebral bone and the implant, i.e. to provide a high resistance to movement between the implant and the vertebral bone, not only an optimal height adjustment of the implant is important but also the angular orientation of the upper and lower implant surfaces that are in contact with the adjacent vertebral bodies plays a crucial role. This is because the contact surfaces of the adjacent vertebral bodies are usually non-planar but rather concave and their orientation often deviates from the horizontal plane. For this reason, modular implants which are assembled from several parts are more often used nowadays. The modular construction allows for attaching different endplates, in particular wedge-shaped endplates with different heights and surface inclinations, to an intermediate implant body. Such a multi-part implant is disclosed, for instance, in US 2014/0156006. The implant comprises at least a bottom endplate, a top endplate and an expandable body in between, whereby the size, height and angulation of each component needs to be chosen in accordance with the patient's individual pathology and anatomical condition.

The disadvantage of such multi-part assemblies is that before inserting the implant into the resected part of the spinal column, the surgeon needs to determine the appropriate implant size and angulation of the endplates in order to allow correct alignment of the implant in relation to the other vertebral bodies. Although prior X-rays or other images give an idea of the required implant size, the exact configuration of the implant needed is often only possible during surgery. As a consequence, multiple sets comprising expandable bodies in different sizes and endplates with different shapes, sizes, heights and angulations need to be prepared, i.e. sterilized and arranged, for each surgery.

The problem solved by the present invention is therefore to provide a vertebral body replacement device which can be inserted and adjusted in situ within a cavity provided by full or partial corpectomy, such that it provides a strong interface between the installed device and the adjacent vertebral bodies to avoid post-surgical dislocation of the device.

This problem is solved by the prosthetic device according to Claim 1. Preferred embodiments are subject of the dependent Claims.

The prosthetic device according to the present invention is a vertebral body replacement device, i.e. an implant for replacing at least part of a vertebral body including one adjacent intervertebral disc. The prosthetic device can be expanded from a fully collapsed state to a fully expanded state. In particular, the prosthetic device can be inserted in its collapsed state into a cavity provided between a first (superior) and a second (inferior) vertebral body by removing at least part of one or more vertebra(e) (complete or incomplete corpectomy). Once positioned in-between the first and second vertebral bodies, the prosthetic device can be expanded and adjusted in situ until optimal fitting of the device and the desired spacing between the adjacent vertebral bodies is achieved. The prosthetic device thereby functions as bridging element in between the remaining vertebral bodies and allows for restoration and stabilization of the natural profile of the spine.

Since the prosthetic device is intended for use within the human body, the terms "upper" and "lower", "anterior", "posterior", "lateral" and "medial", "distal" and "proximal" as used in the context of the present invention have been chosen in accordance with the commonly used anatomical terms of the human body. Nevertheless, it is understood that the present invention relates to the device itself, independent of its positioning within the body. Therefore, as far as the device itself is concerned, these terms primarily serve for differentiation purposes and no limitation of the scope of the invention is thereby intended.

Thus, as far as the prosthetic device is concerned, "medial" refers to a location closer to the midline compared to a "lateral" location, which is farther away from the midline, i.e. towards the side. In addition, when describing the orientation of individual parts of the prosthetic device, reference will be made to the following three basic planes which transect the device:

The frontal plane refers to a vertical plane (i.e. a plane in the x-y direction that is perpendicular to the ground) that cuts the device vertically in half and thereby separates the anterior from the posterior.

The (mid)sagittal plane refers to a vertical plane in the y-z direction that extends perpendicular to the frontal plane and therefore cuts the device vertically in half, thereby separating the proximal from the distal.

The transverse plane refers to a horizontal plane in the x-z direction (i.e. parallel to the ground) which separates the superior from the inferior along the vertical central axis, i.e. an upper position above the transverse plane from a lower position below the transverse plane.

In accordance with the present invention, the prosthetic device is expandable from a fully collapsed state to a fully expanded state and includes:

an anterior end and a posterior end which are located on opposite sides of the vertical frontal plane;

a proximal end and a distal end which are located on opposite sides of the vertical (mid)sagittal plane; and a top end and a bottom end which are located superiorly and inferiorly of the horizontal transverse plane, respectively.

In addition, the prosthetic device comprises an upper endplate having a top surface that is located at the top end and is configured for abutting against a first vertebral body, a lower endplate having a bottom surface that is located at the bottom end and is configured for abutting against a second vertebral body, and an expandable support structure extending between the upper endplate and the lower endplate, said expandable support structure being configured to displace the two endplates relative to one another along a longitudinal vertical axis of the prosthetic device and to hold the two endplates at an axial distance that—in the fully expanded state of the device—corresponds to at least the height of half of a vertebral body and one adjacent intervertebral disc.

The expandable support structure comprises two posts, namely an anterior post and a posterior post, whereby each post having an upper end hingedly connected to the upper endplate and a lower end hingedly connected to the lower endplate. More specifically, a connection area where the upper end of the posterior post is connected to the upper endplate is located in proximity to the posterior end of the device, and a connection area where the upper end of the anterior post is connected to the upper endplate is located in proximity to the anterior end of the device. The posts further have a length defined by the axial distance between the upper end and the lower end of the respective post.

The term "post" is thereby to be understood as an element that may be configured as cylindrical or with any other cross-sectional shape, e.g. rectangular, hexagonal, elliptical, etc. and it may also be formed from multiple parts which are moveably or fixedly connected to each other. Thus, the term "post" may for example also refer to a wall-shaped structure that connects the two endplates.

By adjusting the length of the posts, the overall height of the prosthetic device is also adjusted. The height of the device is hereby defined as the axial distance between the top surface of the upper endplate and the bottom surface of the lower endplate. The axial distance between the two endplates therefore is smallest if the prosthetic device is in the fully collapsed state, and the endplates are held at a maximum distance if the device is in the fully expanded state. From the point of view of the posts this means that the posts are set to a minimal length when the prosthetic device is in the fully contracted or collapsed state and the posts are both set to a maximal length when the device is in the fully expanded state.

Since the prosthetic device of the present invention is for use as a vertebral body replacement and not for merely replacing an intervertebral disc, the height of the device in the fully expanded state must be at least the height of half a human body vertebral body, including one adjacent intervertebral disc. More specifically, in the fully expanded state, the axial distance between the top surface of the upper endplate and the bottom surface of the lower endplate is preferably be at least 2 cm. More preferably, in the fully expanded state, the axial distance between the two endplates is least 2.2 cm, more preferably at least 2.5 cm. In a preferred embodiment, in the fully expanded state of the device, the axial distance between the two endplates is at least 2 cm and at most 12 cm.

In a preferred embodiment, the axial distance between the top surface of the upper endplate and the bottom surface of the lower endplate, i.e. the height of the prosthetic device, can be set to least 1 cm and no more than 12 cm, preferably to at least 1.5 cm and no more than 10 cm, more preferably to at least 2 cm and no more than 7 cm.

Depending on the height of the patient and the location of the vertebral body, i.e. sacral, lumbar, thoracic or cervical, the heights of the vertebral bodies vary to a certain degree. Taking this into account, if only half a vertebral body and one adjacent intervertebral disc is to be replaced, it is preferred that the height of the prosthetic device is adjustable within a range of 1.5 cm to 3 cm. If at least one vertebral body and both adjacent intervertebral discs are to be replaced, the height of the prosthetic device is preferably adjustable within the range of 3 cm to 6 cm. If two vertebral bodies and three intervertebral discs need to be replaced by the prosthetic device of the present invention, the height of the latter is preferably adjustable within the range of 7 cm to 12 cm.

A key aspect of the present invention is that the lengths of the posts, i.e. the lengths of the anterior post and the posterior post, are individually adjustable and are lockable independently from one another. This individual adjustability of the lengths of the posts in combination with the hinged connection provided between the posts and the endplates has the effect that an alteration of the length of one post relative to the length of the other post will cause the endplates to pivot relative to the longitudinal axes of the posts, such that the endplates can be positioned with a certain inclination angle relative to each other. In accordance with the present invention, said inclination angle can be equal or less than 40°.

Thus, by enabling an individual adjustment of the length of the anterior post and the posterior post, respectively, not only the height of the prosthetic device but also the inclination of the endplates relative to each other can be adjusted. More specifically, in line with the present invention, the posts allow for holding endplates at an axial distance from one another that is at least the height of half of a vertebral body and one adjacent vertebral disc (i.e. about 2 cm). At the same time, the length of each post can individually be adjusted and locked within a range that allows for holding the two endplates with an inclination within a range of 0° to 40°, preferably within a range of 0° to 30°, more preferably within a range of 0° to 25°, relative to each other.

With the term "inclination" it is referred to the angle between the plane of the upper endplate and the plane of the lower endplate. Thus, if both endplates are oriented parallel to each other, the inclination angle will be 0°. If the endplates are not oriented parallel, their planes will have a common intersecting line, which is preferably oriented parallel to the horizontal transverse plane of the device. To give a specific example: if the two endplates enclose an inclination angle of 30° relative to each other, one endplate may have an inclination of −10° and the other an inclination of +20° relative to the transverse plane of the device.

The ability to adjust not only the overall height of the implant but also the inclination angle between the endplates is particularly helpful for restoring and stabilizing the natural curvature of the spine, e.g., the angle of lordosis/kyphosis or scoliosis. In addition, this adjustability of the device's configuration in more than one dimension provides for a more universal applicability, which means that the prosthetic device is applicable for use within the cervical, thoracic, lumbar and sacral spine and in a variety of anatomical conditions without requiring assemblage of various components with different diameters, lengths and angulations. In particular, the attachment of additional wedge-shaped top or bottom elements with different heights and surface inclinations to the endplates, such as proposed in US 2014/0156006 for instance, is no longer necessary.

A further advantage of the prosthetic device of the present invention is that it can be implanted in a contracted and therefore compact configuration, which allows for a simple and safe implantation between two vertebral bodies. Once properly accommodated, the prosthetic device can be continuously expanded in situ to support the adjacent vertebral bodies and to restore the natural profile of the spine. In particular, the prosthetic device can be expanded until the desired spacing between the adjacent vertebral bodies is achieved and the posts can then be releasably locked in the selected position. Said locking can be effected, for instance, by the use of locking elements, which will be described in detail further below. The stable positioning of the prosthetic device between the adjacent vertebral bodies ensures that the natural curvature of the spine can be stabilized while maintaining the necessary mobility of the vertebrae to a large extent.

Owing to the provision of at least two posts (instead of just a single one according to various implants of the prior art), the prosthetic device of the present invention allows for better absorption of the mechanical forces acting on the spine when the patient moves. In particular, the prosthetic device can be positioned such that the frontal plane of the device is arranged parallel to the frontal plane of the human body, i.e. such that when implanted between two vertebral bodies of a patient the anterior post is located closer to the anterior side of the spine and the posterior post is located closer to the posterior side of the spine. Thereby, maximum support is provided in the anterior and the posterior regions of the spine—which is where the highest forces occur, in particular during forward or backward bending of the body. Thanks to the provision of an anterior post and a posterior post these forces can be much better absorbed, which makes the prosthetic device less prone to failure through fatigue and wear and also reduces the risk of dislodgement of the device.

Apart from the individual adjustability of the posts, the hinged connection between the posts and the endplates is another key aspect of the present invention. Said hinged connection may theoretically be such that the angular orientation of the two endplates can be adjusted in various directions in relation to the longitudinal axes of the posts. The highest number of degrees of freedom for the angular orientation of the endplates is obtained if the hinged connection between the endplates and the posts is established via universal joints that are provided at each end of the posts: such a post-endplate connection via a universal joint allows for free rotation and pivoting movements of the endplate relative to the posts. However, too many degrees of freedom for the angular adjustment of the endplates and/or the posts can negatively affect the stability of the prosthetic device and make it more difficult to lock the device in the desired configuration.

Therefore, it is preferred that the adjustment of the endplates is restricted to pivoting movements in no more than two directions. More preferably, the endplates are only allowed to pivot about a single pivot axis. This means that it is most preferred that the endplates can be positioned parallel to the transverse plane (horizontal plane in x-z direction) or with an inclination in relation to the latter by pivoting the endplates about the pivot axis.

In a particularly preferred embodiment, the endplates are only allowed to pivot about a pivot axis that extends in the proximal-lateral direction (x-direction). As such, the prosthetic device of the present invention allows to correct a three-dimensional deviation of the spine's curvature in the sagittal plane (vertical plane in y-z direction), i.e. in case of kyphosis or lordosis. It is to be noted that deviations in the frontal plane (vertical plane in x-y direction), i.e. in case of scoliosis, can also be corrected to a certain degree by adjusting the angle of the endplates in relation to the transverse plane.

Once the appropriate spatial and angular configuration of the prosthetic device has been established, the length of the posts can be locked individually to maintain the posts in the selected configuration. Locking of the posts length can be accomplished e.g. by the provision of locking elements, e.g. a screw or a pin, which can be brought from a non-locking position in which the length of the associated can be adjusted, into a locking position in which the length of the associated post is fixed.

Since the inclination of the two endplates relative to each other in the anterior-posterior direction depends on the difference in length of one post relative to the other post, the locking of the posts' length will also lock the angular orientation of the endplates in the sagittal plane. However, depending on the hinged connection provided between the endplates and the posts, pivoting movements of the posts together with the endplates may still be possible. Therefore, the angular orientation of the endplates is preferably not only lockable relative to each other and also relative to the longitudinal axis of the posts. This may be accomplished by the provision of the above-described locking elements for locking the posts or by additional locking elements, which can be brought from a non-locking position in which the orientation of the endplates can be adjusted, into a locking position in which the endplates are angularly fixed.

Although separate locking elements may be provided for locking the angular orientation of the endplates in relation to the longitudinal axis of the posts and in relation to each other, it is more preferred that one or more multifunctional locking element(s) is/are provided, which allow(s) for simultaneously locking the length of the posts and the overall angular orientation of the associated endplates. It is therefore preferred that each post comprises one locking element that can be moved from a non-locking position—in which the length of the post and the orientation of the associated endplate is adjustable—into a locking position—in which the length of the post and the angular orientation of the endplate are both fixed. A more specific embodiment of a prosthetic device involving such multifunctional locking elements will be described in connection with FIG. 9 further below.

In a particularly preferred embodiment of the present invention the prosthetic device comprises at least two shafts that act as connective joints between the endplates and the posts. The shafts allow for providing more stability to the prosthetic device and for facilitating pivotal movements of the endplates.

More specifically, the prosthetic device preferably comprises at least an upper shaft and a lower shaft, wherein the upper shaft hingedly connects the upper endplate with the upper ends of the posts and the lower shaft hingedly connects the lower endplate with the lower ends of the posts. If only two shafts are provided, the posts and the shafts generally extend along the edges of a tetragon, specifically a rectangle. This configuration is particularly advantageous when the prosthetic device is used as replacement device for (part of) a cervical vertebral body, since cervical vertebrae are generally smaller than lumbar vertebrae and the provision of only two shafts allows to make the prosthetic device smaller.

If the prosthetic device is used for replacing at least part of a cervical vertebral body as described above, it is preferred that the shafts are arranged essentially parallel to each other and such that their longitudinal axes lie in the sagittal plane and extend in the anterior-posterior direction. Since the cervical spine is generally accessed via an anterior approach, i.e. through an incision be made on the anterior (frontal) side of the patient's neck, a configuration of the prosthetic device in which the shafts extend in the anterior-posterior direction has the advantage that the anterior ends of the shafts will face the surgeon and can therefore be used for engaging with an expansion tool for adjusting the height of the posts and/or the inclination of the endplates. The ends of the shafts can further be used for attaching a fixation plate—as will be described further below.

In a further preferred embodiment, the prosthetic device comprises at least four shafts, namely at last two upper shafts and two lower shafts, whereby each upper shaft hingedly connects the upper endplate with the upper end of at least one of the at least two posts and each lower shaft hingedly connects the lower endplate with the lower end of at least one of the at least two posts. This configuration is particularly useful if the prosthetic device is used to replace at least a part of a lumbar vertebral body, as it provides the device with additional stability.

If the prosthetic device is used to replace (part of) a lumbar vertebral body, the shafts are preferably arranged essentially parallel to each other and such that their longitudinal axes extend essentially parallel to the frontal plane, i.e. from the distal side of the device to the proximal side. Since the lumbar parts of the spine are generally accessed via an anterior-lateral approach, i.e. the incision will be made on the lateral side of the patient's body. For that reason, configurations in which the shafts extend in the proximal-distal direction are particularly advantageous since the proximal ends of the shafts will face the surgeon and can therefore be used to engage with an expansion tool for adjusting the height of the posts and/or the inclination of the endplates. Again, the end of the shafts may also be used for attaching a fixation plate—this embodiment will be described further below.

The shafts are preferably part of a connective joint that provides the hinged connection between each post and the associated endplate. Said connective joint preferably limits the pivotal and/or rotational degrees of freedom of the endplates with respect to their angular orientation, as this will render the prosthetic device more stable. The prosthetic device can therefore more easily be inserted and repositioned in-situ and locking the device in the desired configuration is also facilitated.

In one embodiment, the connective joint only allows the endplate to pivot in two directions, in particular only about the longitudinal axis of the shaft and about a second pivot axis running perpendicular to the longitudinal axis of the shaft. The pivoting about the longitudinal axis of the shaft can thereby be effected by adjusting the length of the posts independently from one another. The length of the posts is preferably locked by the use of locking elements, which simultaneously also lock the desired angular orientation of the endplates relative to each other and relative to the posts.

In a more preferred embodiment, the connective joint is a hinge joint that only allows the endplate to pivot in one direction, such that the pivoting of the endplates can only be effected by altering the length of one post relative to the other. As a consequence, the angular orientation of the endplates relative to each other is simply locked by locking the posts in their individual (extended) configuration. If the prosthetic device is provided with four shafts, the upper endplate is preferably only allowed to pivot about the longitudinal axes of the two upper shafts and the lower endplate is preferably only allowed to pivot about the longitudinal axes of the two lower shafts.

If the shafts are part of a hinge joint as described above, each endplate preferably comprises at least one socket or receptacle with an opening that is sized and shaped to insertably receive and pivotally hold a portion of one of the shafts therein. The sockets and the shafts are preferably of complementary shape. For instance, if the shafts are cylindrical, the sockets preferably have a cylindrical opening to allow the shafts to pivot about their longitudinal axis when accommodated within the opening. It is further preferred that each shaft is accommodated within a longitudinally extending groove that is formed in the surface of the associated endplate.

In a preferred embodiment, a middle section of each shaft is pivotably held within the opening of a respective socket and is further received along its longitudinal axis in a groove that runs essentially parallel to either the anterior-posterior axis or the proximal-distal axis of the associated endplate. In this embodiment, if the device comprises only two shafts, each endplate comprises one socket. In the case of four shafts, each endplate comprises two sockets.

Alternatively, it is preferred that both end portions of each shaft are pivotably held within a respective socket. More specifically, if the prosthetic device comprises only two shafts, each endplate is preferably provided with two sockets—one in proximity to the anterior end and one in proximity to the posterior end of the device. The openings of the sockets are preferably connected via a groove or depression that extends along the anterior-posterior axis of the respective endplate. If the device comprises four shafts, each endplate preferably comprises two grooves and four sockets, whereby the former preferably extend in the proximal-distal direction between the openings of two associated sockets. Thus, in this case, one groove and the associated two sockets will be located closer to the anterior end of the associated endplate, whereas the other groove and its associated sockets will be located closer to the posterior end. Again, the grooves and the openings of the sockets and are sized and shaped to pivotally receive a portion of a respective shaft therein, such that the shafts are free to pivot around their longitudinal axes when held within the sockets.

It is further particularly preferred that the shafts include a hollow body or at least a hollow portion at one end, preferably at both ends. The provision of hollow shafts (or at least a respective hollow portion at at least one end of each shaft) is beneficial in two ways: On the one hand, it allows for easy attachment of a fixation plate (the purpose of which will be later explained in detail) and on the other hand, it also allows for temporal engagement of an auxiliary expanding tool, e.g. spreading forceps, for expanding or contracting the length of each post.

The tools used for inserting the device into a patient's body are preferably angled since this facilitates handling of the device within the patient's body.

In a specifically preferred embodiment, the shafts comprise a hollow outer body with an essentially circular cross-section and an inner hollow rod having a non-circular, e.g. oval, cross-section. The cross-section of the inner hollow rod therefore has a larger and a smaller diameter. The larger diameter of the inner rod is smaller than the diameter of the outer body, which allows the inner rod to rotate about its longitudinal axis within the outer body. In the space between the inner surface of the outer body and the outer surface of the inner rod, locking elements are spring-mounted. In a non-locking position, the locking elements are positioned on an axis extending along the smaller diameter of the inner rod. If the inner rod is rotated about its longitudinal axis, the diameter of the inner rod at the location of the locking elements increases and causes locking elements to move against the spring force towards the outer body into a locking position, in which adjustment of the length of the associated post and adjustment of the angular position of the endplate in relation to the associated post are simultaneously prohibited. The locking elements may for example be bolts or pins that can be moved from a non-locking (resting) position against the spring-force into a groove in the outer body. In this locking position, i.e. when the locking elements are positioned within the groove, the length of the posts and the angular orientation of the endplates are locked. An exemplary embodiment of such locking elements is described herein in connection with FIG. 9.

Except for the fixation plate(s)—if applicable—the prosthetic device is preferably preassembled before its implantation. This facilitates insertion of the device and reduces the risk of losing one of the parts of the device during implantation. For implanting the device, the latter is preferably locked in the fully collapsed state. This allows that an expansion tool, e.g. a spreading forceps, can be opened in between the two endplates or posts to hold the prosthetic device.

Preferred embodiments regarding the functional design of the posts and the mechanisms involved in the length adjustment of each post are described in the next sections. For the sake of simplification, in the following paragraphs, there will be no distinction between the anterior post and the posterior post, but it will rather generally be referred to "the post" in singular.

In a preferred embodiment, each post comprises an inner extension member, which is positioned coaxially and at least partly within an outer sleeve-like member. The length of the post is thereby adjustable by axial movement of the inner extension member with respect to the outer sleeve-like member. The inner extension member is may for example be telescopically or slidably movable with respect to the outer sleeve-like member, preferably with the aid of a mechanically, hydraulically or pneumatically driven actuator.

The inner and outer members generally have cross-sections of similar shape. They may have circular or rectangular cross-sections or, alternatively, cross-sections of any geometric shape.

In a preferred embodiment, the posts comprise an inner extension member having threads on its outer surface and further comprise an outer sleeve-like member with interior threads for engaging with the outer threads of the inner extension member. Rotation of either the inner or the outer member results in the expansion or the collapse of the post due to the outer sleeve-like member and the inner extension member moving in opposite directions along their central axis. For instance, in case of the inner and outer member being in a screw engagement, a driver may be used to operably engage with one of the members for torque transmission.

Instead of a screw engagement, the outer sleeve-like member may comprise a plurality of slots on an inner surface facing the inner extension member and the latter has on its outer surface one or more teeth, spikes or jagged edges that is/are engaged in the slots. (Naturally, the slots may also be provided on the inner extension member and the teeth or other protrusions on the outer sleeve-like member.) In a preferred embodiment, the length adjustment of the post can be accomplished with the assistance of spreading forceps. To this end, the working ends of the spreading forceps are preferably brought into engagement with the proximal ends of the upper and lower endplates. This way, the length of the post can be adjusted by simply opening or closing of the forceps.

The inner extension member may alternatively be moveable relative to the outer member by use of a manually operated actuator device. As a further alternative, the inner extension member may be movable with the assistance of a rack that is rotated by a removable force transmission tool. As another alternative, the inner extension member may be hydraulically or pneumatically extractable with respect to the outer sleeve-like member.

More preferably, the prosthetic device comprises at least two shafts as described above and these shafts are preferably provided with a hollow shaft portion, e.g. a longitudinal bore, at their ends. As such, the working ends of spreading forceps can be inserted into the hollow shaft portions in order to establish a temporal engagement between the shafts and the spreading forceps for adjusting the length of the posts and/or the angular orientation of the endplates.

As indicated earlier, the posts may also have a non-circular cross-section but rather the cross-section of a regular or irregular polygon, e.g. triangle, rectangle, square . . . . In a preferred embodiment, the posts are wall-shaped and extend along the anterior and posterior side of the device, respectively. The anterior and the posterior sides of the prosthetic device are thus closed, whereas the proximal and distal sides of the device are freely accessible. This embodiment has the benefit that the wall-shaped posts provide a particularly strong support structure along the anterior and the posterior side of the spine. The term "wall-shaped" in this embodiment means that the posts have a greater length and height than width (or thickness). For instance, it is preferred that the walls have a length (measured in the proximal-distal direction) within the range of 16-32 mm, more preferably 19-28 mm, and a wall thickness within the range of 0.5-5 mm, preferably 1-3 mm. The expandable posts therefore form a more or less rectangular housing with two walls facing one another and two open sides. Contrary to a normal house, the walls are hingedly connected to the upper and lower endplate, forming the roof and the base floor or the house. To allow expansion of each post, the wall-shaped posts may comprise an outer sleeve-like member and an inner extension member as described above. Alternatively, each wall-shaped post may comprise two walls that are coaxially engaged and can slide along each other.

With regard to the orientation of the posts, it is preferred that the anterior post and the posterior post extend essentially parallel to one another. One example would be the above-described embodiment involving wall-shaped posts. To hingedly connect parallel extending posts with the associated endplates it is particularly preferred that the prosthetic device comprises at least two shafts as described above. For instance, for replacing a sacral, lumbar or thoracic vertebral body the prosthetic device preferably comprises four shafts that are oriented parallel to the frontal plane, wherein the upper end of the anterior post is connected with an upper anterior shaft and the lower end of the anterior post is connected with a lower anterior shaft. In analogy thereto, the upper end of the posterior post is then connected with an upper posterior shaft and the lower end of the posterior post is connected to a lower posterior shaft.

However, the anterior and the posterior posts may alternatively also extend along the diagonals of a rectangle or a cube, such that they have a common intersection in the center of the prosthetic device. This embodiment is preferred if the prosthetic device is to be used for replacing a cervical vertebral body. In this case, the prosthetic device preferably comprises two shafts oriented parallel to the sagittal plane (i.e. in the anterior-posterior direction), such that the upper ends of the anterior and posterior posts are connected with an upper shaft and the lower ends of both posts are connected with a lower shaft. The posts therefore extend along the diagonals of a rectangle that lies in the sagittal plane.

Although the prosthetic device of the present invention has been mostly described by embodiments comprising at least two posts, it goes without saying that the expandable support structure may also comprise at least three posts or at least four posts. More than two posts are preferred if additional strength must be provided, e.g. for patients that intend to continue with heavy physical work or high-performance sport. Embodiments in which the prosthetic device comprises only two posts have the advantage that fewer parts need to be adjusted and locked.

Independent from the number of posts, it is generally preferred that the upper endplate and the lower endplate are connected to each other by means of the posts only. The connection between the posts and the endplates does not have to be direct but will generally be via an intermediate hinge. An indirect connection of the posts and the endplates is for example a connection of these elements via intermittent shafts. However, it is preferred that no additional cages or support structures are present for connecting the two endplates. This ensures that sufficient space is available in between the endplates for placing a considerable volume of bone grafts, or substitutes thereof, and for ingrowth of newly-formed bone and tissue material.

In a particularly preferred embodiment, the prosthetic device further comprises at least one flange-like fixation plate, preferably two fixation plates, for fixedly attaching the device to an adjacent vertebral body (or adjacent vertebral bodies). By providing one or more fixation plate(s) that connect(s) the prosthetic device with the adjacent vertebra (e), the contact area between the prosthetic device and the bone structure of adjacent vertebral bodies is increased, which provides secure support to and firm anchoring of the device within the spine. In particular, the fixation plate(s) ensure(s) that any rotational movements around the longitudinal axis of the device with respect to the adjacent vertebral bodies—and therefore also any rotation of the adjacent vertebral bodies with respect to each other—can be securely prohibited. This means that the prosthetic device, once installed, can neither move sideways nor rotate around its longitudinal middle axis. In consequence, the risk of sinking or a misplacement of the prosthetic device is greatly reduced.

In a preferred embodiment, the fixation plate extends upwardly from the upper endplate or downwardly from the lower end plate (i.e. in each case in a direction away from the center of the prosthetic device). Depending on the side of the surgical approach, the fixation plate(s) is/are attached to the proximal or anterior side of the device. If the prosthetic device is to replace a cervical vertebral body, the approach will generally be from the anterior side and the fixation plate will therefore be attached to the anterior side of the device. On the other hand, if the prosthetic device is installed to replace a lumbar vertebral body via a lateral or anterior-lateral approach, the fixation plate will be attached to the proximal side of the device.

In any case, the fixation plate generally comprises at least one through-hole for receiving a fixation member therethrough. In the implanted state, the through-hole faces the adjacent vertebral body, thereby allowing insertion of a fixation member through the through-hole and into the bone tissue of the adjacent vertebral body. Preferably, the through-hole is a threaded through-hole, i.e. configured as a threaded bore, and the fixation member is configured as a retaining screw. The fixation plate is further preferably provided with a lateral curvature such that it can be aligned with the curvature of the periphery of the vertebral body against which it is to be secured.

To provide a particularly high stability, it is particularly preferred that the prosthetic device comprises two fixation plates, namely an upper fixation plate extending from the upper endplate towards the associated adjacent vertebral body and a lower fixation plate extending from the lower endplate towards the associated adjacent vertebral body. This allows for a fixation of the prosthetic device to both adjacent vertebral bodies (i.e. the first and the second vertebral body), which provides a particularly stable positioning of the prosthetic element, also under high mechanical load occurring during bending or turning movements of the spine. This is of high importance since implants of the kind of the present invention often stay within the patient's body for a long time and must therefore be able to cope with high mechanical loads occurring during daily activities and sports. In addition, the provision of two fixation plates as described above prevents rotation of the upper and lower vertebral bodies in relation to the prosthetic device and in relation to one another. Such rotational movements of the vertebral bodies greatly increase the risk of mispositioning of the device and must therefore be avoided.

Each fixation plate preferably has a lateral curvature that approximates the curvature of the periphery of the adjacent vertebral body against which it is to be secured. Preferably, the upper fixation plate is similarly configured to the lower fixation plate, but extends essentially in an opposite direction.

For attaching the fixation plate(s) to the device, many alternative ways are possible. For instance, in one embodiment, a base plate is attached or integrally formed with the fixation plate and projects in a more or less perpendicular direction from an edge of the fixation plate. As a result, if viewed from the side, the fixation plate and the base plate have an L-shaped configuration. The base plate is wedge-shaped and tapers in the direction away from the fixation plate. The endplate to which the fixation plate is to be attached comprises a slot that matches the wedge-shape of the base plate, such that the latter can be inserted into the slot and held within the slot by a friction fit. In the assembled state, the base plate extends essentially parallel to the associated endplate and the fixation plate extends from the proximal or anterior end of said endplate in the direction of the adjacent vertebral body.

In a preferred embodiment, the prosthetic device comprises at least two shafts as described further above and the shafts are used to attach the fixation plate to the prosthetic device. The fixation plate is thereby preferably attached to the proximal or anterior end(s) of the upper shaft (s) or the lower shaft(s). For use within the cervical region of the spine, the prosthetic device preferably comprises two shafts that are arranged essentially parallel to the frontal plane, the fixation plate is preferably attached to the proximal ends of the upper shafts or the lower shafts. On the other hand, for use within the lumbar area of the spine, i.e. if an anterior-lateral or lateral surgical approach is used and the shafts are therefore preferably arranged essentially parallel to the sagittal plane, the fixation plate is preferably attached to the anterior ends of the upper shaft(s) or the lower shaft(s). The attached fixation plate thereby preferably extends essentially perpendicular to the longitudinal axis of the shaft in a direction towards the adjacent vertebral body and comprises at least one through-hole, preferably a threaded through-hole, for allowing insertion of a fixation member therethrough, e.g. a screw or nail, to attach the fixation plate to the adjacent vertebral body.

If four shafts are involved, the attachment of the fixation plate to the ends of the associated shafts is thereby preferably accomplished by one of the two ways described in the following:

In one preferred embodiment, the at least one through-hole of the fixation plate is provided in proximity to a first end of the fixation plate. In proximity to a second end, which is arranged opposite to the first end, the fixation plate comprises two additional openings (through-holes). Said openings are preferably symmetrically disposed on either side of a midline of the fixation plate. Said openings may either have a cross-section that is slightly larger than the cross-section of the shafts, such that the latter can be inserted through the openings to seat the fixation plate on the shafts. In an alternative preferred embodiment, the shafts are provided with a hollow shaft portion at the proximal (or anterior) end and the cross-section of the openings in the fixation plate corresponds to the cross-section of the hollow end portions of the shafts. This allows for an attachment of the fixation plate via screw- or nail-like fixation elements that are inserted through the openings of the fixation plate and into the hollow shaft end portions of the associated shafts.

The fixation elements are preferably releasably held in the hollow proximal (or anterior) end portions, e.g. by screwing or simply inserting them into the hollow shaft end portions. In case of a screwing engagement, it is preferred that the openings and the hollow proximal (or anterior) end shaft portions comprise corresponding interior screw threads, such that the fixation plate can be attached to the proximal ends of the shafts by inserting a fixation screw through the fixation plate and into the hollow end shaft portion. Alternatively, the fixation elements may also be held inside the hollow shaft portions via a gluing or press-fit engagement.

The fixation elements may either be separate fixation elements that are inserted through openings in the fixation plate and then into the hollow proximal (or anterior) end shaft portions as described above, or they may be an integral part of the fixation plate, i.e. fixedly attached thereto, e.g. in the form of pins projecting away from the surface of the fixation plate. In this case, the fixation elements are preferably simply inserted into the hollow end portions of the associated shafts or they may also be glued, friction-locked or press-fitted therein if desired.

In a preferred embodiment, the fixation elements attached to the prosthetic device together with the fixation plate. This may either be accomplished by first inserting the fixation elements through the openings in the fixation plate and then as one unit to the prosthetic device or by having the fixation elements fixedly attached to or integrally formed with the fixation plate. It is thereby particularly preferred that the fixation elements are hollow, e.g. having a hollow cylindrical body. Hollow fixation elements are beneficial as they allow for a guide-wire to be inserted through the fixation elements (e.g. outside the patient's body) and into the hollow end portions of the shafts (e.g. after having the device implanted into the patient's spine). This way, the surgeon may simply slide the fixation plate together with the fixation elements along the guide-wire until the latter are inserted into the hollow shaft end portions. The risk of losing a fixation element or misplacing the fixation plate is thereby greatly reduced.

If the hollow end portions of the shafts are to be used as a retention portion for temporally engaging with the working ends of an expanding tool, e.g. a spreading forceps, for adjusting the length of the post(s) and/or the angular orientation of the endplate(s) as described above, it goes without saying that this adjustment is usually accomplished before insertion of the fixation elements into the hollow end portions of the shafts.

If two fixation plates are provided, one is preferably attached to the upper shaft(s) and one attached to the lower one(s).

The components of the prosthetic device are preferably made from biocompatible materials including metals, high density plastics, thermofusible polymer material, in particular PEEK (polyether ether ketone), carbon fiber and ceramics. Carbon and PEEK have the advantage that they are radiolucent, i.e. X-ray permeable, and therefore allow x-ray viewing of the intervertebral space and position of the vertebral bodies subsequent to implantation of the prosthetic device. Metals or metal alloys, in particular stainless steel, titanium or titanium alloys, such as e.g. $TiAl_6V_4$, on the other hand, are highly suitable implant materials due to their high durability, rigidity, stain-resistance, bacteria-resistant, chemical inertness and oxidation resistance.

In a preferred embodiment, the prosthetic device essentially consists of a metal or a metal alloy that is compatible with magnetic resonance imaging, such as titanium, such that they may be visualized after implantation using X-ray technology.

Alternatively, the components of the inventive device may be made of biodegradable materials (e.g., polyglycolic acid) which are slowly degraded by the body's enzymes. Biodegradable materials, however, must remain present in stable form sufficiently long to allow bone grafts to consolidate.

To further enhance osteointegration of the device and new bone formation through and/or around the prosthetic device, the latter can further be filled and/or coated with bone growth stimulating substances (e.g., osteoblast-stimulating factor) and/or bone grafts to enhance the fusion bone-mass. In this respect, the inventive design of the prosthetic device has the benefit that it provides a large cavity in between the two endplates, which can be filled with bone graft material.

In a preferred embodiment, the bone graft material comprises INFUSE® Bone Graft, which contains recombinant human bone morphogenetic protein-2 (rhBMP-2). rhBMP-2 is a manufactured version of naturally occurring protein BMP-2 that is important for bone formation and healing. In addition, some grinded bone material of the patient (e.g. from the patient's rips and bone mass from the damaged vertebral body that is to be replaced) is preferably added to the bone graft material. Allograft material and/or anti-inflammatory substances, such as antibiotics, may be comprised as well.

The large free internal space available within the prosthetic device, i.e. the space confined by the two end plates on the one hand and the at least two posts on the other hand, allows for placing a considerable volume of bone grafts, or substitutes thereof, and facilitates the transport of blood and nutrients through prosthetic device once implanted, thereby reducing inflammatory reactions and possible rejection reactions. In particular, blood supply can be preserved via one of the two segmental arteries (intercostal arteries) that supplement the blood flow to the spinal cord. For instance, if the prosthetic device is inserted via a lateral surgical approach from the proximal side into the spine of a patient, the proximal segmental artery needs to be cut, but the distal segmental artery can be preserved, which guarantees that cells involved in building up tissue receive sufficient nutrients and oxygen.

As regards the functional design of the endplates, it is preferred that the upper endplate and/or the lower endplate comprise(s) a window to permit bone cell ingrowth. More preferably, the endplates may have a "mesh"- or grid-like structure, allowing a wide diffusion of the growing bone cells into the interior space between the two endplates of the prosthetic device. Such bone cell ingrowth is favourable to complete osteointegration of the implant.

Since each endplate is intended to bear against the surface of an associated vertebral body, they are preferably shaped complementary to the respective vertebral body surface. In general, the surface that is intended to bear against an associated vertebral body is provided with a slightly convex curvature. Thanks to the individual adjustability of the posts, the inclination of the endplates can be adjusted, such that wedge-shaped endplate attachment elements (often called "caps") are no longer necessary for adapting the prosthetic device to match the positional orientation of the associated vertebral body.

Also, the top surface of the upper endplate and the bottom surface of the lower endplate may further comprise a structuring, e.g. a barb, teeth or small spikes, in order to obtain an improved mechanical connection between the vertebral body and the implant. Thereby, the risk of dislocation of the prosthetic device after its expansion in between the first and the second vertebral body can be reduced.

Figure 2:
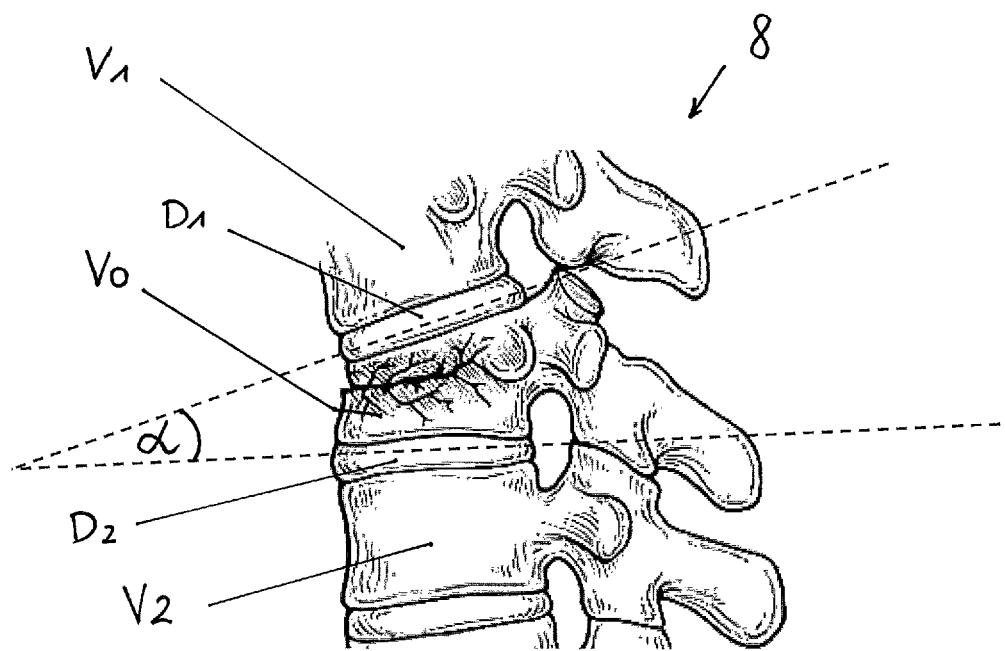
Figure 3:
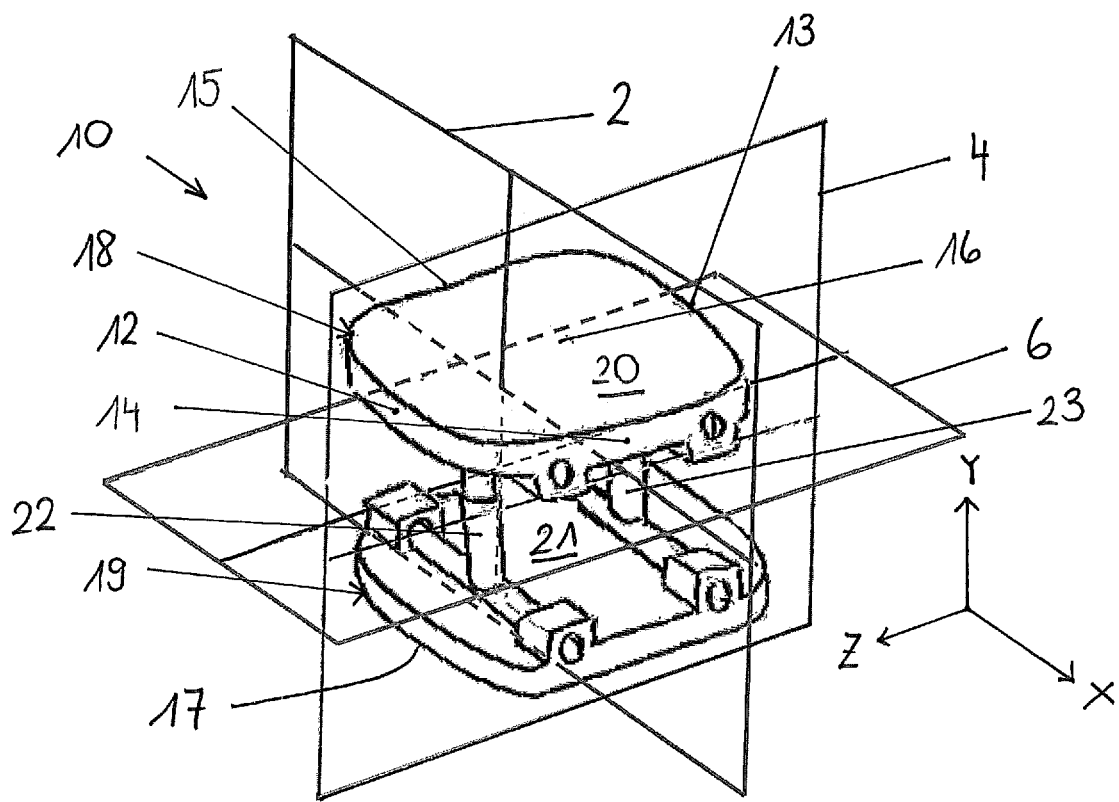
Figure 4:
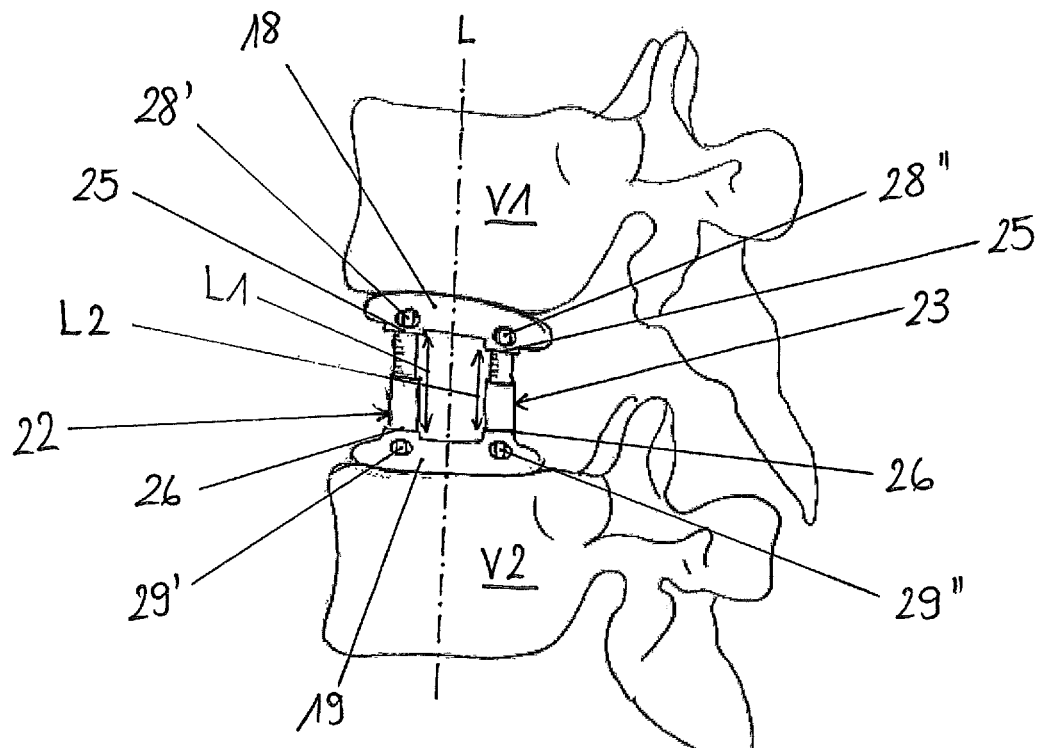
Figure 5:
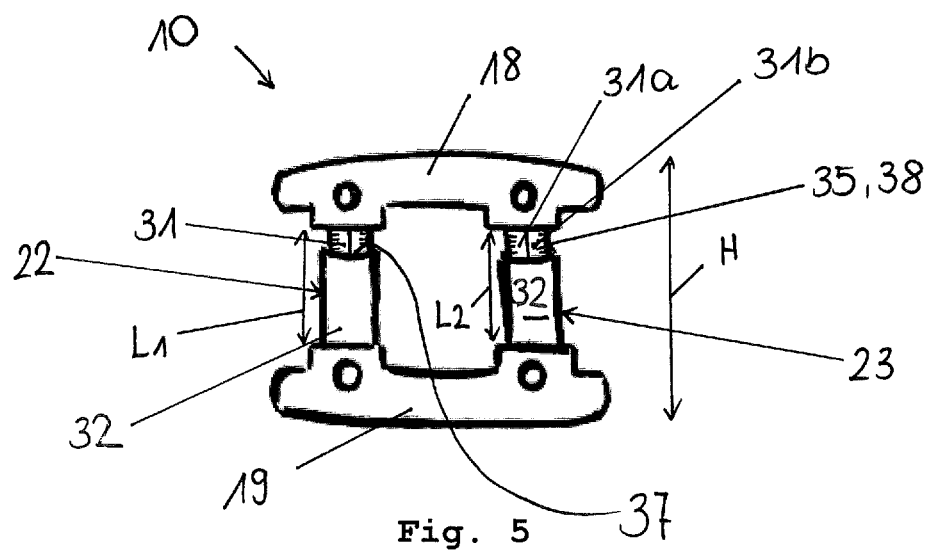
Figure 6:
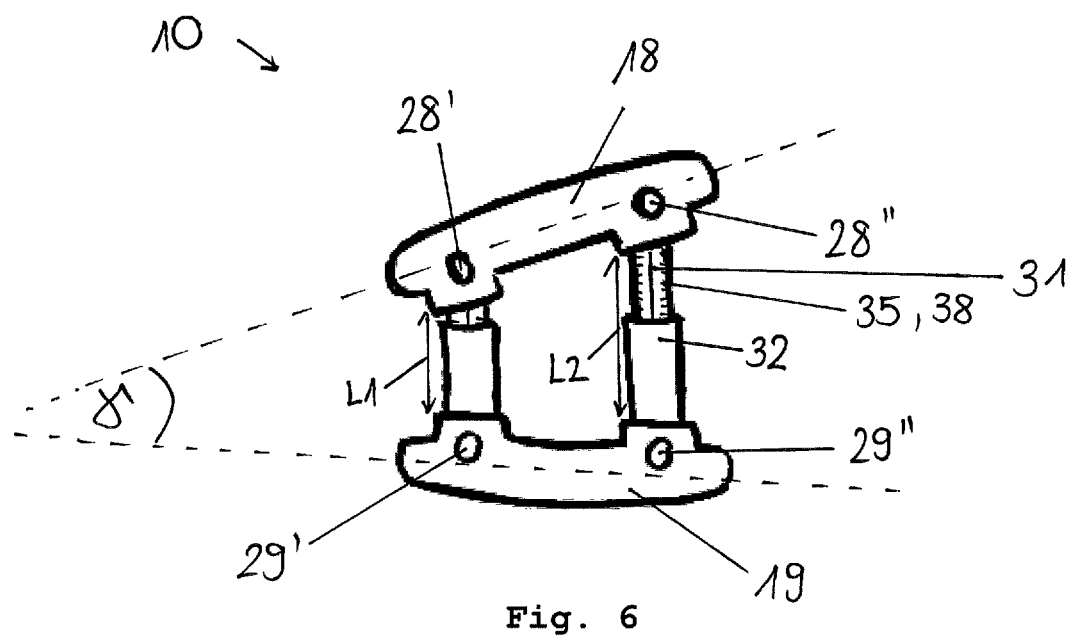
Figure 7:
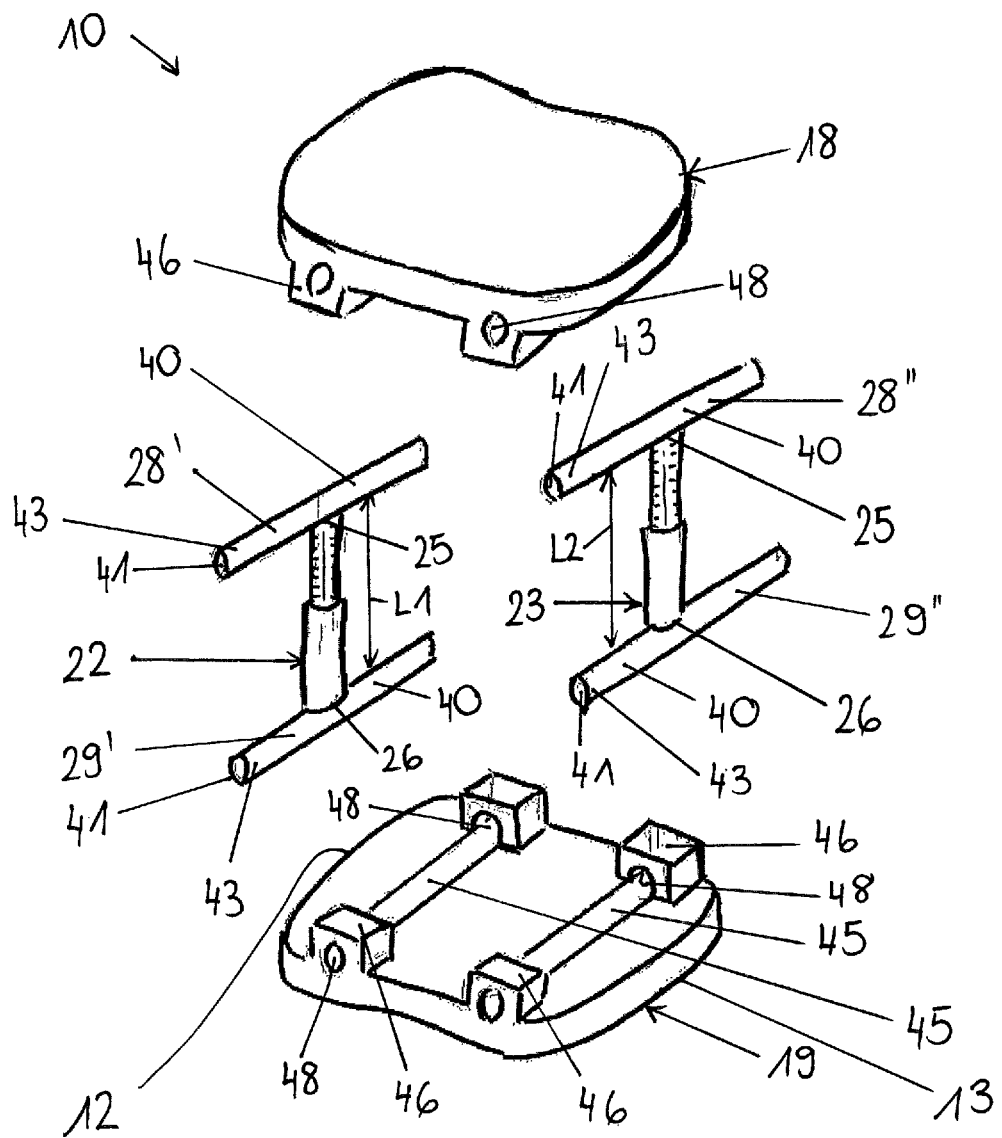
Figure 8:
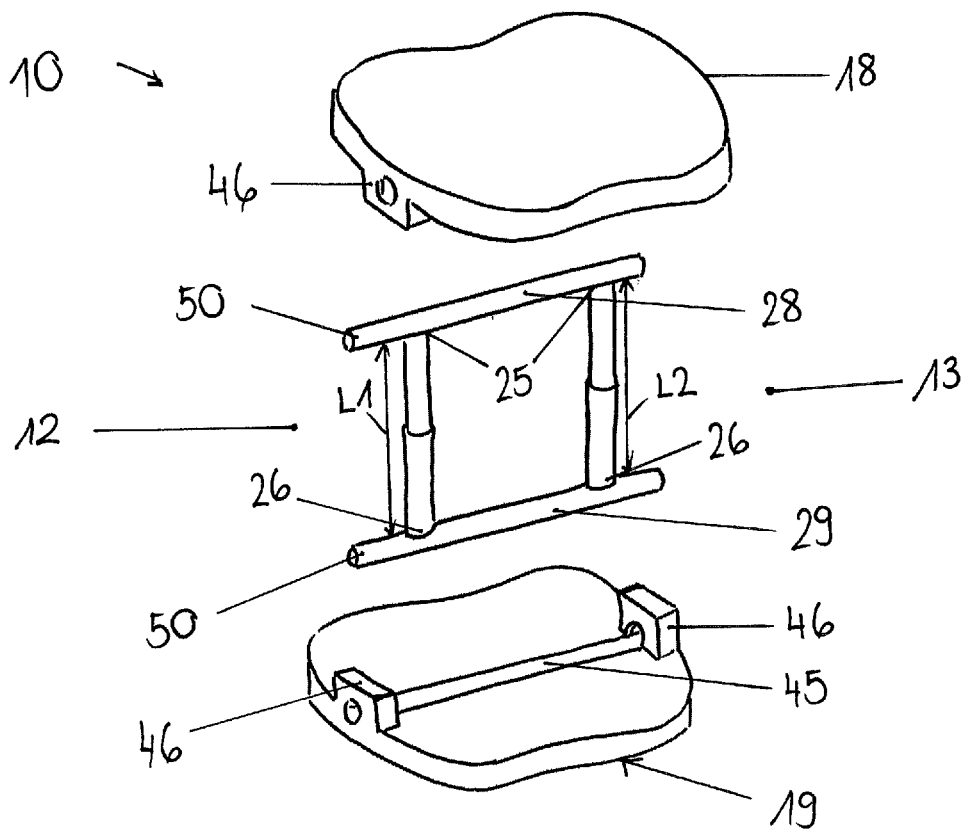
Figure 9:
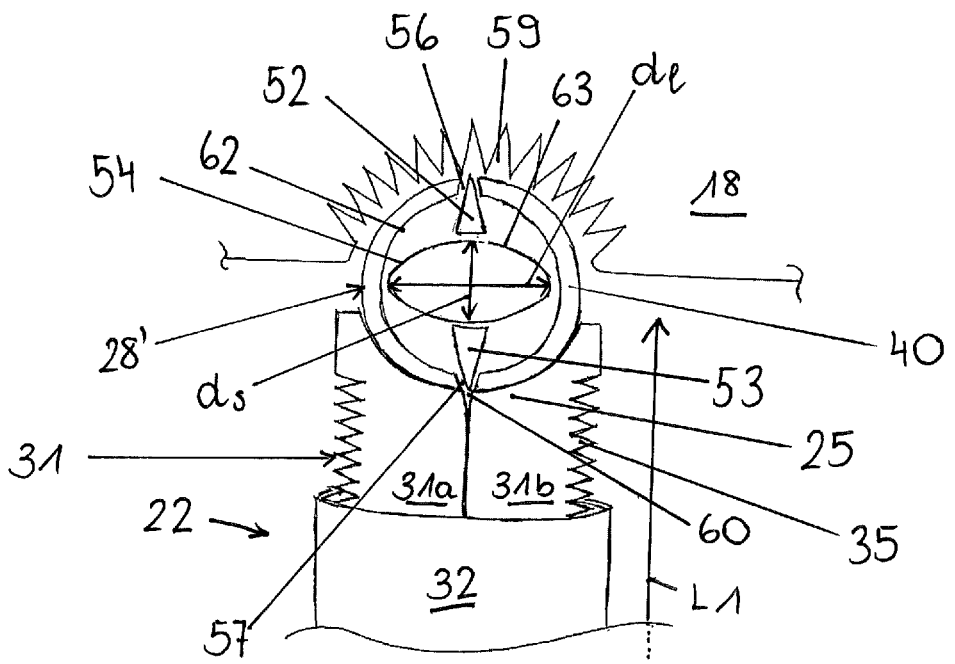
Figure 10:
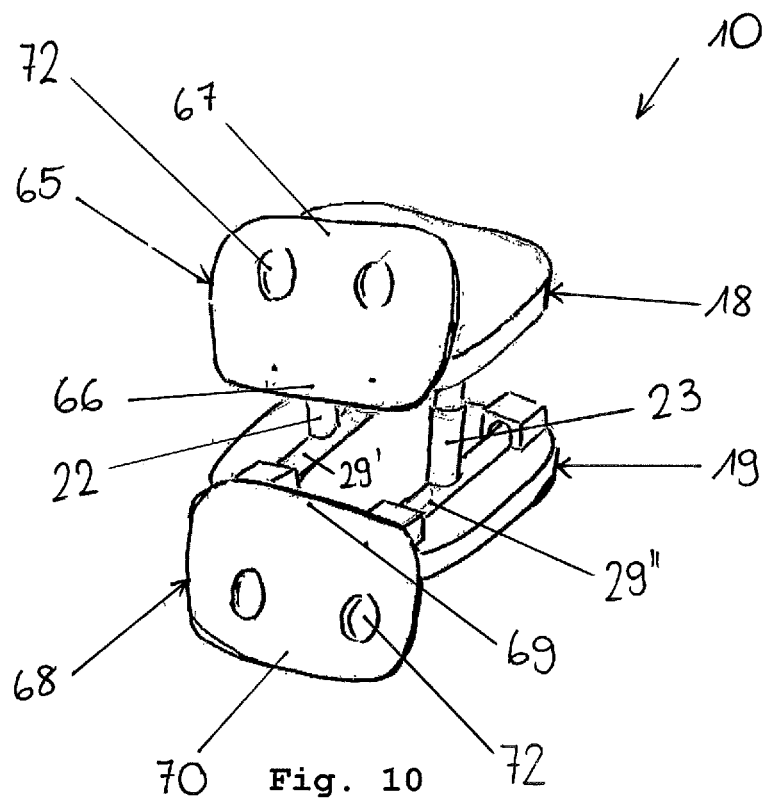
Figure 11:
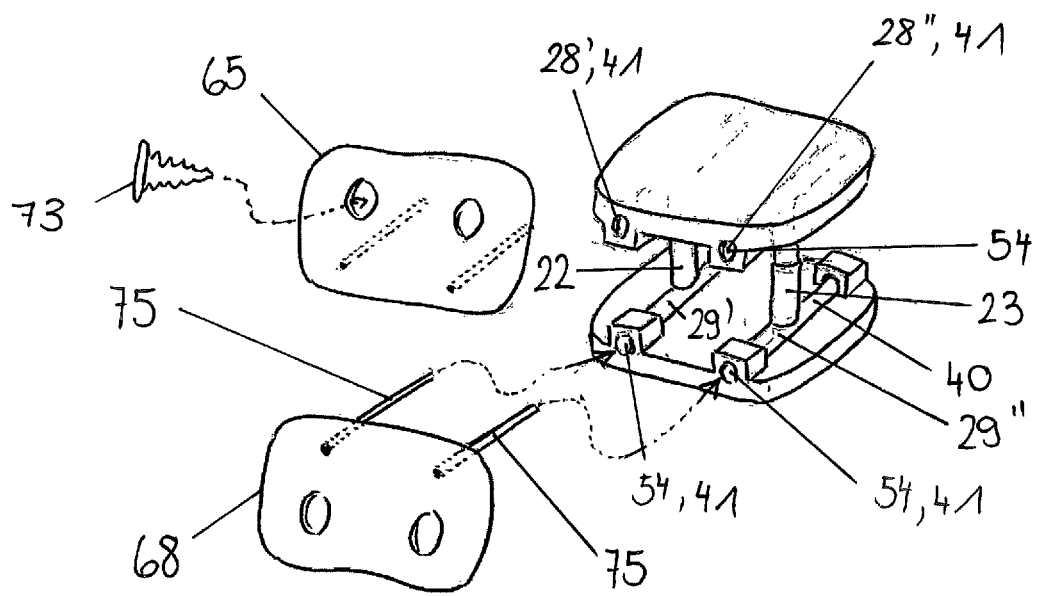

Particularly preferred embodiments of the present invention are described below and illustrated in the drawings in which purely schematically show:

FIG. 1 perspective view of a human body and the anatomical planes;

FIG. 2 a perspective view of a segment of a lumbar spine including a vertebral body having a compression fracture;

FIG. 3 a perspective view of an embodiment of the prosthetic device according to the present invention and with the anatomical planes of the human body of FIG. 1 transecting the device in the implanted state;

FIG. 4 a sectional view of the prosthetic device of FIG. 3 in its expanded state and locked configuration within a space formed between two adjacent vertebral bodies of a spine;

FIG. 5 a perspective view of the prosthetic device of FIG. 3 in a fully collapsed state;

FIG. 6 a perspective view of the prosthetic device of FIG. 3 in a partially expanded state;

FIG. 7 a perspective exploded view of the prosthetic device of FIG. 3;

FIG. 8 a perspective exploded view of an alternative embodiment of the prosthetic device;

FIG. 9 an enlarged cross-sectional view of an upper anterior section of the prosthetic device of FIGS. 3-7;

FIG. 10 a perspective view of the prosthetic device of FIG. 3 and two fixation plates attached to the device;

FIG. 11 a perspective view of the prosthetic device of FIG. 10 with the two fixation plates to be attached.

In anatomy, there are three basic planes that transect the human body. In FIG. 1 is shown how these basic planes transect a human body:

The coronal or frontal plane 2 is an Y-X plane (i.e. a vertical plane that is perpendicular to the ground) and separates the anterior from the posterior.

The (mid)sagittal plane 4 is an Y-Z plane (i.e. perpendicular to the ground) that is exactly in the middle of the body and separates left from right within the human body. With respect to the prosthetic device 10 in the implanted state (shown in FIG. 4), said midsagittal plane 4 also separates the proximal side from the distal side of the device.

The transverse plane 6 is an X-Z plane (i.e. a horizontal plane that is parallel to the ground) and separates an upper or superior portion from a lower or inferior portion—e.g. the head from the feet.

FIG. 2 shows a segment of a patient's spine 8 with one damaged vertebral body V0 that is to be replaced by a prosthetic device 10 of the present invention (see FIG. 3).

If the damaged vertebral body V0 and the adjacent vertebral discs D1 and D2 are removed by a corpectomy procedure, a cavity is provided within the upper and lower remaining vertebral bodies V1 and V2. This is where a prosthetic device 10 of the present invention is to be placed (see FIG. 4). Thus, the prosthetic device 10 is used to replace at least a part of the damaged vertebral body V0 as well as its associated subjacent and suprajacent discs D1 and D2. The overall dimension of the prosthetic device 10 is therefore such that it is dimensioned to fit within the cavity provided by the corpectomy procedure.

From FIG. 2 it is further shown that the collapsed vertebral body V0 causes a change in the curvature of the spine 8, which is generally accompanied by severe pain. Therefore it is essential that the prosthetic device 10 not only fills the empty space between the remaining vertebral bodies V1 and V2 after the corpectomy, but also allows for restoring and stabilizing the natural curvature of the spine 8, in particular the angle α of lordosis/kyphosis or scoliosis.

FIG. 3 shows an embodiment of a prosthetic device 10 of the present invention, together with the three basic planes of the human body of FIG. 1 transecting the device when it is in the implanted state (shown in FIG. 4). As mentioned, the prosthetic device 10 is intended for use as a vertebral body replacement device that acts as a spaceholder for at least one vertebral body or at least part thereof removed from the spine. In general terms prosthetic device 10 comprises:

an anterior end 12 and a posterior end 13 which are located on opposite sides of the vertical frontal plane 2;

a proximal end 14 and a distal end 15 which are located on opposite sides of the vertical midsagittal plane 4 arranged perpendicular to the frontal plane 2; and a top end 16 and a bottom end 17 which are located superiorly and inferiorly of the horizontal transverse plane 6, respectively.

The prosthetic device 10 further comprises an upper endplate 18 having an top surface 20 that is located at the top end 16 and is configured for abutting against the first vertebral body V1 (see FIG. 4);

a lower endplate 19 having a bottom surface 21 that is located at the bottom end 17 and is configured for abutting against the second vertebral body V2 (see FIG. 4);

and further comprises an expandable support structure extending between the upper endplate 18 and the lower endplate 19 to maintain an axial space between the two endplates 18, 19. The expandable support structure is configured to displace the upper and the lower endplates 18, 19 relative to one another along a longitudinal axis L of the device 10 (see FIG. 4) and comprises an anterior post 22 and a posterior post 23.

In the implanted state—shown in FIG. 4—the posterior post 23 is positioned in closer proximity to the spinal cord, i.e. posteriorly of the frontal plane 2, and the anterior post 22 is positioned anteriorly of the frontal plane 2. Although in the shown embodiment the posts 22, 23 have a cylindrical shape, it should be understood that other shapes and configurations of the posts 22, 23 are also contemplated. For example, in other embodiments of the invention, the posts 22, 23 may have other cross-sectional shapes, such as, for example, rectangular, hexagonal or elliptical cross-sectional shapes. In particular, the posts 22, 23 may also be shaped as walls, i.e. structures that have a rectangular cross-section.

As can be seen from FIG. 4, each post 22/23 has an upper end 25 that is hingedly connected to the upper endplate 18 via an upper shaft 28', 28" and each post 22/23 further has a lower end 26 hingedly connected to the lower endplate 19 via a lower shaft 29', 29" (best see e.g. in FIGS. 6 and 7). Thus, each post 22/23 has a length L1/L2 defined by the axial distance between the upper end 25 and the lower end 26 of the respective post 22/23. Yet, as will be explained in more detail in connection with FIGS. 5 and 6, the length L1/L2 of each post 22/23—and thereby the overall height of the prosthetic device 10—is individually adjustable, which means that the lengths L1, L2 of the posts 22, 23 can be adjusted independently from one another.

In general, the endplates 18, 19 have a width (in the proximal-distal direction) and length (in the anterior-posterior direction) that corresponds to the width and length of the vertebral body V0 that is to be replaced. Naturally, the endplates 18, 19 may be made smaller for smaller statured patients or for smaller regions of the cervical spine, e.g. in embodiments of the prosthetic device being associated with the upper thoracic or cervical region of the spine. Also, larger endplates may be useful to provide a larger support in cases of osteoporosis, and smaller endplates in cases of vertebral fractures where only a part of a vertebral body is to be replaced.

In addition, the endplates 18, 19 do not necessarily have to be identical but they may be shaped and sized differently from one another and/or they may be provided with different texturing on their bone-engaging surface.

Usually, the prosthetic device 10 is implanted in its fully contracted and therefore compact configuration (see FIG. 5). This allows for a simple and safe implantation of the device 10 between the two adjacent vertebral bodies V1, V2. Once properly accommodated, the prosthetic device 10 can be continuously expanded in situ to support the adjacent vertebral bodies V1, V2 and to restore the natural profile of the spine. This in situ adjustability of the prosthetic device 10 has the advantage that it is easy to place or insert and permits an optimal, tight fit and correction of the deformity within the affected spinal area by in vivo expansion of the device.

In terms of the present invention, this means that by adjusting the length L1, L2 of the posts 22, 23, the prosthetic device 10 can be adjusted from a fully collapsed to fully expanded configuration. More specifically, the prosthetic device 10 may be expandable to an overall maximum height that is at least two times the height of the device in the collapsed state. In general, the overall height H of the prosthetic device 10 can be adjusted from a minimum height in the range of about 2 cm to a maximum height of about 10 cm.

As best seen in FIGS. 5 and 6, each post 22/23 comprises an inner extension member 31, which is slidably disposed within an outer sleeve-like member 32. The inner extension member is formed by two identical racks 31a, 31b that have a plurality of plurality teeth 35 on an outer surface 38. The teeth 35 face a plurality of slots 34 (not visible) provided on an inner wall surface 37 of the outer sleeve-like member 32.

Each post 22/23 further comprises a locking element 53 (shown in FIG. 9), which allows for independently locking or securing the respective post 22/23 in a certain expanded configuration. More specifically, if the locking element 53 is in a non-locking position, the teeth 35 on the outer surface 38 of the inner extension member 31 are not engaged in the slots 34 on the inner wall surface 37 of the outer member 32 and the length L1/L2 of the respective post 22/23 is freely adjustable by axial movement of the inner extension member 31 with respect to the outer sleeve-like member 32. The axial movement of the inner extension member 31 may be achieved e.g. by the aid of an expansion instrument, such as spreading forceps (not shown). If the locking element 53 (see FIG. 9) is in a locking position, the teeth 35 of the inner extension member 31 engage in the slots 34 of the outer sleeve-like member 32, which has the effect that the length L1/L2 of the post 22/23 is fixed and the latter can neither collapse nor expand any further.

As shown in FIG. 6, not only the overall height H of the prosthetic device 10 but also the inclination angle α between the endplates 18, 19 of the prosthetic device 10 can be adjusted.

More specifically, if both posts 22, 23 are expanded to an equal length L1=L2, the two endplates 18, 19 are held in a parallel orientation. This is also the case in the collapsed state shown in FIG. 5. However, since the length L1/L2 of each post 22/23 can be adjusted independently from one another and since a hinged connection is provided between the posts 22, 23 and the endplates 18, 19, the angular orientation of the two endplates 18, 19 can also be non-parallel and the angular positioning of the endplates 18, 19 relative to each other can be adjusted by adjusting the length L1/L2 of one post 22/23 relative to the other 23/22.

In the shown embodiment the hinged connection is established via the shafts 28', 28", 29', 29" (also see FIGS. 7 and 8), such that the endplates 18, 19 are only allowed to pivot about a pivot axis that runs parallel to the longitudinal axes of the shafts 28, 29. As a result, an expansion of the posterior post 23 results in a gradual increase in height H of the device 10 from the anterior end 12 to the posterior end 13, as depicted in FIG. 6. In the shown partially expanded state, the inclination angle α between the two endplates 18, 19 is about 30°.

In accordance with the present invention, the individual adjustability of the length L1/L2 of each post 22/23 allows for holding the two endplates 18, 19 with an inclination of 0° to 40° relative to each other. Thereby, the prosthetic device 10 of the present invention allows to correct a three-dimensional deviation of the spine's curvature in the sagittal plane 4 (vertical plane in y-z direction), i.e. in case of kyphosis or lordosis. It is to be noted that deviations in the frontal plane 2 (vertical plane in x-y direction), i.e. in case of scoliosis, can also be corrected to a certain degree by adjusting the angular positioning of the endplates 18, 19 in relation to the transverse plane 6 (see FIG. 3).

Thanks to the possibility to adjust not only the length L1, L2 of the posts 22, 23 but also the angular orientation of the endplates 18, 19, the prosthetic device 10 is applicable for use within the cervical, thoracic, lumbar and sacral spine and in a variety of anatomical conditions without requiring assemblage of various components with different diameters, lengths and angulations. In particular, the attachment of additional wedge-shaped top or bottom elements with different heights and surface inclinations to the endplates is no longer necessary.

On the other hand, an adjustability of two variables also means that the prosthetic device 10 must either be provided with two separate locking means, i.e. locking means for locking the posts 22, 23 in their individual expanded length L1, L2 and additional locking means for locking the desired angular orientation of the endplates 18, 19 relative to each other, or the device comprises locking means that allow for locking both variables at the same time—an example of such locking means will be discussed in more detail in connection with FIG. 9.

As can be best seen from the exploded view shown in FIG. 7, the prosthetic device 10 of FIG. 3 comprises four shafts, namely an upper anterior shaft 28' and an upper posterior shaft shafts 28" as well as a lower anterior shaft 29' and a lower posterior shaft 29". The shafts 28', 28", 29', 29" each comprise a hollow outer cylindrical body 40 and are arranged essentially parallel to one another and are oriented such that their longitudinal axes extend essentially parallel to the frontal plane 2 (see FIG. 3), i.e. from the distal side of the device 10 to the proximal side.

In the shown embodiment, the upper end 25 of the posterior post 23 is fixedly connected to the upper posterior shaft 28" and the upper end 25 of the anterior post 22 is fixedly connected to the upper anterior shaft 28'. The upper endplate 18 is hingedly connected to both upper shafts 28', 28", i.e. to the upper posterior 28' and also to the upper anterior shaft 28". In the same way, the lower ends 26 of the posts 22, 23 are connected to the lower endplate 19 via the intermediate lower posterior shaft 29" and the lower anterior shaft 29', respectively. Because the posts 22, 23 are fixedly, i.e. rigidly, connected to the associated shafts 28', 29' or 28", 29", the endplates 18, 19 are only allowed to pivot about the longitudinal axes of the shafts and said pivotal movement is only possible if the length L1/L2 of at least one post 22/23 is adjusted accordingly. Thus, in the shown embodiment, the shafts 28', 28", 29', 29" function as a hinge joint and only permit pivoting of the endplates 18, 19 by altering the length L1/L2 of one post 22/23 relative to the other 23/22. As a consequence, the angular orientation of the endplates 18, 19 is simply locked by locking the posts 22, 23 in their individual (extended) configuration. The device 10 thereby is provided with additional stability, which facilitates insertion and in-situ repositioning thereof.

An orientation of the shafts 28', 28", 29', 29" in the distal-lateral direction is particularly useful if the prosthetic device 10 is used to replace (part of) a lumbar or sacral vertebral body: Since the lumbar or sacral parts of the spine are generally accessed via an anterior-lateral approach, i.e. the incision will be made on the lateral side of the patient's body. If the shafts 28', 28", 29', 29" extend in the proximal-distal direction the proximal ends 41 of the shafts will therefore face the surgeon and can be used for adjusting the length L1, L2 of the posts 22, 23 and/or the inclination of the endplates 18, 19 relative to each other. Hollow end portions 43 that are present at the proximal ends 41 of the shafts 28', 28", 29', 29" can thereby serve as retention portions for temporally engaging with the working ends of an expanding tool, e.g. a spreading forceps, (not shown) for adjusting the length L1/L2 of the posts 22/23. Specifically, the working ends of the expanding tool can be inserted into the hollow end portions 43 and the tool can be opened or closed for adjusting the length L1/L2 of the associated post 22/23. Furthermore, the shafts 28', 28", 29', 29" can also be used for attaching a fixation plate, as will be described later in connection with FIGS. 10 and 11.

In FIG. 7 it is further visible that each endplate 18, 19 comprises two grooves 45 and four sockets 46. One of the two grooves 45 of each endplate 18, 19 is provided in proximity to the anterior end 12 and the other one in proximity to the posterior end 13 of the device 10. In the shown embodiment, the basic shape of the grooves 45 is a longitudinally open cylinder and one socket 46 is provided at the opposite ends of each groove 45.

Each socket 46 functions as receptacle and has an opening 48 that is sized and shaped to insertably receive and pivotally hold a portion of one of the shafts 28', 28", 29', 29" therein. This means that the openings 46 have an inner diameter that is slightly larger than the diameter of the associated shaft 28'/28"/29'/29" in order to allow rotation of the shafts 28', 28", 29', 29" about their longitudinal axis once accommodated within the socket(s) 46. The ends of each groove 45 run into the opening 48 of the associated sockets 46, such that the openings 48 form a tunnel, the base of which being formed by the groove 45 and the walls being formed by the respective socket 46.

In the embodiment shown in FIG. 8, the prosthetic device 10 comprises only two shafts, namely an upper shaft 28 and a lower shaft 29, wherein the upper shaft 28 hingedly connects the upper endplate 18 with the upper ends 25 of the posts 22, 23 and the lower shaft 29 hingedly connects the lower endplate 19 with the lower ends 26 of the posts 22, 23. The posts 22, 23 and the shafts 28, 29 therefore extend along the edges of a rectangle. In order to allow the length L1, L2 of the posts 22, 23 to be adjusted individually and independently from one another, a hinged connection must at least be provided between the shaft 28/29 and the associated ends 25/26 of the posts 22, 23 (i.e. between the upper shaft and the upper end 25 of each post 22, 23 as well as between the lower shaft 29 and the lower end 26 of each post 22, 23). In the embodiment of FIG. 8 each endplate 18, 19 comprises one groove 45 and two sockets 46. One of the two sockets 46 of each endplate 18, 19 is provided in proximity to the anterior end 12 and the other one in proximity to the posterior end 13 of the device 10.

The embodiment of the prosthetic device 10 shown in FIG. 8 is particularly suitable for replacing at least part of a cervical vertebral body: In this embodiment, the shafts 28, 29 are arranged essentially parallel to each other and such that their longitudinal axes lie in the sagittal plane 4 (see FIG. 1), such that they extend in the anterior-posterior direction. Since the cervical spine is generally accessed via an anterior approach, i.e. through an incision made on the anterior (frontal) side of the patient's neck, a configuration of the prosthetic device 10 in which the shafts 28, 29 extend in the anterior-posterior direction has the advantage that hollow shaft portions provided at the anterior ends 50 of the shafts 28, 29 will face the surgeon and can therefore be serve as retention portions for engaging the tip of a tool (not shown) that is used to adjust the lengths L1, L2 of the posts 22, 23 and/or the inclination of the endplates 18, 19. The anterior ends 50 of the shafts 28, 29 can further be used for attaching a fixation plate (see FIGS. 10 and 11).

FIG. 9 shows an enlarged cross-sectional view of the upper anterior shaft 28' of the embodiment shown in FIGS. 3-7. The shaft 28' is hingedly connected with the upper endplate 18 on the one hand and fixedly connected with the upper end 25 of the anterior post 22 on the other hand.

In the embodiment shown in FIGS. 3-7, the shafts 28', 28", 29', 29" are part of a locking assembly that allows for simultaneously locking the adjusted lengths L1, L2 of the posts 22, 23 and the angular orientation of the endplates 18, 19 in relation to each other and in relation to the posts 22, 23. Thus, once the appropriate height of the prosthetic device and the desired angular orientation of the endplates 18, 19 have been set, the device 10 can be secured in this configuration by moving locking elements 52, 53 of the locking assembly from a "non-locking position" depicted in FIG. 9 into a "locking position".

As better visible in FIG. 7, the anterior upper shaft 28' is accommodated along its longitudinal axis within a respective groove 45 formed in the associated endplate 18. The shaft 28' comprises a hollow outer body 40 with a circular cross-section and an hollow inner rod 54 having an oval cross-section. Owing to the oval cross-section the hollow inner rod 54 has therefore a larger diameter $d_r$ and a smaller diameter $d_s$. The larger diameter $d_r$ of the inner rod 54 is smaller than the diameter of the outer body 40, which allows the inner rod 54 to rotate about its longitudinal axis within the outer body 40. In a connection area, where the shaft 28' is connected with the associated post 22 at the one hand and with the associated endplate 18 at the other hand, the outer hollow cylindrical body 40 of each shaft 28' is provided with two openings, namely a top opening 56 and a bottom opening 57 that are located opposite each other along the extended longitudinal axis of the associated post.

The top opening 56 of the outer body 40 leads into one of a plurality of top nuts 59 provided in the upper endplate 18 and the bottom opening 57 leads into a bottom nut 60 provided in the upper end 25 of the post 22. More specifically, the bottom nut 60 is disposed in between the two racks 31a, 31b of the inner extension member 31.

In the space between the inner wall surface 62 of the outer body 40 and the outer wall surface 63 of the inner rod 54, two locking elements 52, 53 are spring-mounted adjacent to the top and bottom openings 56, 57, on opposite sides of the inner rod 54. In the non-locking (resting) position, the locking elements 52, 53 are positioned on an axis extending along the smaller diameter of the inner rod 54. In this non-locking position, the length L1 of the post 22 can be freely adjusted and the associated endplate 18 is allowed to pivot about the longitudinal axis of the associated shaft 28'. If the inner rod 54 is rotated 90° about its longitudinal axis, the locking elements 52, 53 will be pressed against the spring force through the top opening 56 and the bottom opening 57 into the top nut 59 and the bottom nut 60, respectively. In this locking position, the locking elements 52, 53 are disposed in the respective nut 59, 60 and are positioned on an axis extending along the larger diameter $d_r$ of the inner rod 54. Insertion of the associated locking element 52 into the top nut 59 will lock the angular position of the endplate 18 in relation to the post 22. On the other hand, insertion of the associated locking element 53 into the bottom nut 60 will cause the two racks 31a, 31b of the inner extension member 31 to move apart, such that the teeth 35 of both racks 31a, 31b will engage in the slots 34 of the sleeve-like member 32. Engagement of the teeth 35 of the inner extension member 31 within the slots of the outer sleeve-like member 32 will lock the position of the inner extension member 31 within the sleeve-like member 32 of the associated post 22, such that the length L1 of the post 22 cannot be adjusted anymore.

Rotation of the inner hollow rod 54 can be effected for example by the insertion of the end of a flat screw driver tool into an end portion of the hollow rod 54. The same hollow end portion can also be used for engaging the tips of an expanding tool (not shown) to adjust the length L1 of the post 22 and/or for inserting fixation means to attach a fixation plate, as will be described in the following.

As shown in FIG. 10, the prosthetic device 10 can further comprise one or more fixation plate(s) 65, 68 for fixedly attaching the device 10 to an adjacent vertebral body V1/V2 (see FIG. 4).

The fixation plate 65/68 increases the contact area between the prosthetic device 10 and the adjacent vertebral body V1/V2, which provides secure firm anchoring of the device 10 within the spine. In particular, any rotational movements around the longitudinal axis of the device 10 with respect to the adjacent vertebral bodies V1, V2 and therefore also any rotation of the adjacent vertebral bodies V1, V2 with respect to each other can be securely prohibited. A stable positioning of the prosthetic device 10, even under high mechanical load occurring during bending or turning movements of the spine, is particularly important, since prosthetic devices of the kind of the present invention often stay within the patient's body for a long time and must therefore be able to sustain such loads over a prolonged time period.

In the shown embodiment an upper fixation plate 65 is attached to the proximal ends 41 of the two upper shafts 28', 28" and a lower fixation plate 68 is attached to the proximal ends 42 of the two lower shafts 29', 29" (see FIG. 11). Both fixation plates 65, 68 extend essentially perpendicular to the longitudinal axis of the shafts 28', 28", 29', 29" in a direction away from a center of the prosthetic device 10. Thus, the fixation plates 65, 68 extend in opposite directions; the upper fixation plate 65 extends upwards towards the superior adjacent vertebral body V1 and the lower fixation plate 68 extends downwards towards the inferior adjacent vertebral body V2 (see FIG. 4).

Each fixation plate 65/68 has a first end 66/69 adjacent the associated endplate 18/19 and a second end 67/70 located opposite the first end 66/69 and therefore remote from the associated endplate 18/19. In proximity to the second end 67/70, each fixation plate 65/68 comprises two respective threaded through-holes 72. These through-holes 72 are provided for receiving a fixation member 73 (see FIG. 11), in particular a fixation screw, therethrough to attach the fixation plate 65/68 to the associated adjacent vertebral body V1/V2.

The fixation plates 65/68 are preferably provided with a lateral curvature such that it can be aligned with the curvature of the anterior periphery of the vertebral body V1/V2 against which it is to be secured.

FIG. 11 shows an embodiment in which the fixation plates 65, 68 are not yet attached to the prosthetic device 10. As can be seen in this view, the device comprises four shafts 28', 28", 29', 29" having each an outer hollow body 40 and an hollow inner rod 54 as described in connection with FIG. 9. The fixation plates 65, 68 are hereby to be attached to the proximal ends 41, 42 of the associated shafts 28', 28"/29', 29". To this end, each fixation plate 65/68 comprises two respective pins 75 that are fixedly attached or integrally formed with the associated fixation plate 65/68 and project away therefrom at an essentially right angle.

For attaching the fixation plates 65, 68 to the associated shafts 28', 28", 29', 29", the pins 75 are inserted into the hollow inner rods 54 (indicated for the fixation plate 68 with dashed lines). The pins 75 may be simply inserted into the hollow inner rods 54 or they may be additionally secured therein by gluing or press-fit engagement. The pins 75 of the fixation plates 65, 68 itself are also hollow and are provided with an oval cross-section that is slightly smaller than the cross-section of the hollow inner rods 54. The orientation of the pins 75 attached to the fixation plates 65, 68 is such that it matches the orientation of hollow inner rods 54 in the locking position. Thereby, insertion of the pins 75 into the hollow rods 54 and subsequent fixation of the fixation plates 65, 68 to the associated vertebral body V1/V2 will also prohibit rotational movement of the inner rods 54 within the outer bodies 40 of the shafts 28', 28", 29', 29", such that the locking elements 52, 53 shown in FIG. 9 will remain in the locking position after attachment of the fixation plates 65, 68.

The benefit arising from the provision of pins 54 that are hollow is that this design allows for a guide-wire (not shown) to be inserted through the pins 54 (outside the patient's body) and into the hollow end portions 55 of the inner rods 54 (after having the device implanted into the patient's spine). This way, the surgeon may simply slide the fixation plate 65/68 along the guide-wire until the pins 75 are inserted into the hollow inner rods 54.

It goes without saying that the length adjustment of the posts 22, 23 via the shafts 28', 28", 29', 29" will generally occur before the attachment of the fixation plates 65, 68, as the end portions 55 of the hollow inner rods 54 will in the above-described embodiment be occupied by the pins 75 after attaching the fixation plates 65,68.

While the preferred embodiments shown in the Figures comprise only two expandable posts 22, 23, three, four or even more expandable posts can be provided. Naturally, the expandable posts 22, 23 may also have another shape than the cylindrical shape depicted. The same applies for the upper and lower endplates 18/19: they may have a variety of shapes and they may be essentially planar or convexly curved to complement the contoured surface of a vertebral body endplate.

The invention claimed is:

1. A prosthetic device for replacing at least one vertebral body, the prosthetic device being expandable from a fully collapsed state to a fully expanded state and having
    an anterior end and a posterior end which are located on opposite sides of a vertical frontal plane;
    a proximal end and a distal end which are located on opposite sides of a vertical midsagittal plane arranged perpendicular to the frontal plane; and
    a top end and a bottom end which are located superiorly and inferiorly of a horizontal transverse plane, respectively,
wherein the prosthetic device further comprises
    an upper endplate having a top surface that is located at the top end and is configured to abut against a first vertebral body,
    a lower endplate having a bottom surface that is located at the bottom end and is configured to abut against a second vertebral body, and
    an expandable support structure extending between the upper and lower endplates, said expandable support structure being configured to displace the two endplates relative to one another along a longitudinal axis of the prosthetic device and to hold the two endplates at an axial distance that is measured between the top surface of the upper endplate and the bottom surface of the lower endplate and corresponds to the height of at least half a vertebral body and one intervertebral disc,
    wherein the expandable support structure includes an anterior post and a posterior post, each post having an upper end hingedly connected to the upper endplate and a lower end hingedly connected to the lower endplate and each post having a length which is defined by the axial distance between the upper end and the lower end of the respective post,
    wherein the length of each post is individually adjustable and is lockable independently from one another to hold the two endplates with an inclination of 0° to 40° relative to each other,
wherein the prosthetic device further comprises at least one upper shaft and at least one lower shaft, wherein the upper shaft hingedly connects the upper endplate with the upper ends of the posts, the lower shaft hingedly connects the lower endplate with the lower ends of the posts, and the upper and lower shafts are arranged essentially parallel to one another and are oriented such that their longitudinal axes extend essentially parallel to the frontal plane or the sagittal plane.

2. The prosthetic device according to claim 1, wherein the axial distance between the top surface of the upper endplate and the bottom surface of the lower endplate is within a range of 1.5 cm to 12 cm.

3. The prosthetic device according to claim 2, wherein the axial distance between the top surface of the upper endplate and the bottom surface of the lower endplate is within a range of 3 cm to 6 cm.

4. The prosthetic device according to claim 2, wherein the axial distance between the top surface of the upper endplate and the bottom surface of the lower endplate is within a range of 7 cm to 12 cm.

5. The prosthetic device according to claim 1, comprising at least two upper shafts and two lower shafts, whereby each upper shaft hingedly connects the upper endplate with the upper end of at least one of the posts, and each lower shaft hingedly connects the lower endplate with the lower end of at least one of the posts.

6. The prosthetic device according to claim 1, wherein the hinged connection between the endplates and the posts is such that each endplate is only pivotable about a pivot axis running parallel to and/or an axis running perpendicular to a longitudinal axis of one of the shafts.

7. The prosthetic device according to claim 6, wherein the hinged connection between the endplates and the posts is such that each endplate is only pivotable about either a pivot axis running parallel to or an axis running perpendicular to a longitudinal axis of one of the shafts.

8. The prosthetic device according to claim 1, wherein each post comprises an inner extension member positioned coaxially with and at least partly within an outer sleeve-like member, such that the length of each post is adjustable by axial movement of the inner extension member with respect to the outer sleeve-like member.

9. The prosthetic device according to claim 8, wherein the inner extension member is movable with respect to the outer sleeve-like member with the aid of a mechanically, hydraulically or pneumatically driven actuator.

10. The prosthetic device according to claim 1, wherein the posts extend essentially parallel to one another and are wall-shaped with an essentially rectangular cross-section.

11. The prosthetic device according to claim 1, wherein the upper endplate and the lower endplate are connected to each other by means of the posts only.

12. The prosthetic device according to claim 1, wherein the shafts comprise a hollow essentially cylindrical outer body and a hollow inner rod having a non-circular cross-section, wherein the inner rod can be rotated about its longitudinal axis within the outer body to move at least one locking element from a non-locking position in which the length of the associated post is freely adjustable and the associated endplate is allowed to pivot about the longitudinal axis of the shaft, into a locking position in which the desired length of the post and the angular position of the endplate relative to the post is locked.

13. The prosthetic device according to claim 1, further comprising at least one fixation plate which extends from an edge of one of the endplates and approximately perpendicular thereto in a direction away from the other endplate, wherein the fixation plate comprises at least one through-hole for receiving a fixation member therethrough.

14. The prosthetic device according to claim 1, further comprising at least one fixation plate, which is attached to an end of at least one of the shafts and which extends essentially perpendicular to a longitudinal axis of the shaft in a direction away from the other endplate, wherein the fixation plate comprises at least one through-hole for receiving a fixation member therethrough.

15. The prosthetic device according claim 14, wherein the fixation plate is attached to the end of at least one of the shafts by a pin inserted into a hollow shaft portion at the end of said shaft.

16. The prosthetic device according to claim 1, wherein at least one of the endplates comprises a window or a grid-like structure for allowing the ingrowth of bone cells.

17. A prosthetic device for replacing at least one vertebral body, the prosthetic device being expandable from a fully collapsed state to a fully expanded state and having
   an anterior end and a posterior end which are located on opposite sides of a vertical frontal plane;
   a proximal end and a distal end which are located on opposite sides of a vertical midsagittal plane arranged perpendicular to the frontal plane; and
   a top end and a bottom end which are located superiorly and inferiorly of a horizontal transverse plane, respectively,
wherein the prosthetic device further comprises
   an upper endplate having a top surface that is located at the top end and is configured to abut against a first vertebral body,
   a lower endplate having a bottom surface that is located at the bottom end and is configured to abut against a second vertebral body,
   an expandable support structure extending between the upper and lower endplates, said expandable support structure being configured to displace the two endplates relative to one another along a longitudinal axis of the prosthetic device and to hold the two endplates at an axial distance that is measured between the top surface of the upper endplate and the bottom surface of the lower endplate and corresponds to the height of at least half a vertebral body and one intervertebral disc, and
   at least one fixation plate which extends from an edge of one of the endplates and approximately perpendicular thereto in a direction away from the other endplate, the fixation plate comprising at least one through-hole for receiving a fixation member therethrough,
   wherein the expandable support structure includes an anterior post and a posterior post, each post having an upper end hingedly connected to the upper endplate and a lower end hingedly connected to the lower endplate and each post having a length which is defined by the axial distance between the upper end and the lower end of the respective post, and
   wherein the length of each post is individually adjustable and is lockable independently from one another to hold the two endplates with an inclination of 0° to 40° relative to each other.

18. A prosthetic device for replacing at least one vertebral body, the prosthetic device being expandable from a fully collapsed state to a fully expanded state and having
   an anterior end and a posterior end which are located on opposite sides of a vertical frontal plane;
   a proximal end and a distal end which are located on opposite sides of a vertical midsagittal plane arranged perpendicular to the frontal plane; and
   a top end and a bottom end which are located superiorly and inferiorly of a horizontal transverse plane, respectively,
wherein the prosthetic device further comprises
   an upper endplate having a top surface that is located at the top end and is configured to abut against a first vertebral body,
   a lower endplate having a bottom surface that is located at the bottom end and is configured to abut against a second vertebral body, and
   an expandable support structure extending between the upper and lower endplates, said expandable support structure being configured to displace the two endplates relative to one another along a longitudinal axis of the prosthetic device and to hold the two endplates at an axial distance that is measured between the top surface of the upper endplate and the bottom surface of the lower endplate and corresponds to the height of at least half a vertebral body and one intervertebral disc,
   wherein the expandable support structure includes an anterior post and a posterior post, each post having an upper end hingedly connected to the upper endplate and a lower end hingedly connected to the lower endplate and each post having a length which is defined by the axial distance between the upper end and the lower end of the respective post,
   wherein the length of each post is individually adjustable and is lockable independently from one another to hold the two endplates with an inclination of 0° to 40° relative to each other, and
   wherein at least one of the endplates comprises a window or a grid-like structure for allowing the ingrowth of bone cells.

\* \* \* \* \*